with fluorescent probes", BBA, 871 (1986) (pp. 61-71)—XP009061712.

(12) United States Patent
Stark et al.

(10) Patent No.: US 9,366,677 B2
(45) Date of Patent: Jun. 14, 2016

(54) METHODS FOR ANALYZING BIOLOGICAL MACROMOLECULAR COMPLEXES AND USE THEREOF

(75) Inventors: Holger Stark, Waake (DE); Ashwin Chari, Goettingen (DE); David Haselbach, Cottbus (DE); Jan-Martin Kirves, Goettingen (DE)

(73) Assignee: Max-Planck-Gesellshaft zur Foerderung der Wissenschaften e.V., Munich (DE)

( * ) Notice: Subject to any disclaimer, the term of this patent is extended or adjusted under 35 U.S.C. 154(b) by 48 days.

(21) Appl. No.: 14/241,502

(22) PCT Filed: Sep. 6, 2011

(86) PCT No.: PCT/EP2011/004475
§ 371 (c)(1),
(2), (4) Date: Feb. 27, 2014

(87) PCT Pub. No.: WO2013/034160
PCT Pub. Date: Mar. 14, 2013

(65) Prior Publication Data
US 2014/0206092 A1      Jul. 24, 2014

(51) Int. Cl.
*G01N 33/68*    (2006.01)
*G01N 21/64*    (2006.01)
*G06F 19/16*    (2011.01)

(52) U.S. Cl.
CPC ........ *G01N 33/6803* (2013.01); *G01N 33/6845* (2013.01); *G06F 19/16* (2013.01); *G01N 21/6428* (2013.01)

(58) Field of Classification Search
CPC ... G01N 21/64; G01N 21/6428; G01N 33/68; G01N 33/6803; G01N 33/6845; G01N 33/92; G06F 19/16; Y10T 436/143333
USPC ........................ 436/71, 86, 94, 147, 164, 172; 422/82.05, 82.08, 82.12; 702/27, 28, 702/32
See application file for complete search history.

(56) References Cited

U.S. PATENT DOCUMENTS

| | | | | |
|---|---|---|---|---|
| 6,020,141 | A * | 2/2000 | Pantoliano | B01L 7/00 435/4 |
| 2001/0003648 | A1 * | 6/2001 | Pantoliano | C40B 30/04 435/4 |
| 2006/0110732 | A1 | 5/2006 | Bone et al. | |
| 2014/0315190 | A1 * | 10/2014 | Bornarth | G01N 33/582 435/6.1 |

FOREIGN PATENT DOCUMENTS

| | | |
|---|---|---|
| WO | WO 99/24050 | 5/1999 |
| WO | WO 02/103321 | 12/2002 |
| WO | 2010/109204 | * 9/2010 |

OTHER PUBLICATIONS

Kopec et al. Journal of Structural Biology, vol. 175, Apr. 23, 2011, pp. 216-223.*
Stathopulos, P.B., et al., "Calorimetric Analysis of Thermodynamic Stability and Aggregation for Apo and Holo Amyotrophic Lateral Sclerosis-associated Gly-93 Mutants of Superoxide Dismutase", Jr. Biological Chemistry, vol. 281, No. 10, Mar 10, 2006 (pp. 6184-6193).
Dao-Thi, M-H, et al., "The Thermodynamic Stability of the Proteins of the ccd Plasmid Addiction System", JMB, (2000) 299 (pp. 1373-1386).
Di Nardo, A.A., et al., "The Relationship Between Conservation, Thermodynamic Stability and Function in the SH3 Domain Hydrophobic Core", JMB, (2003) 333, (pp. 641-655).
Mezzasalma, T.M., et al, "Enhancing Recombinant Protein Quality and Yield by Protein Stability Profiling", J. of Biomolecular Screening, 12(3), 2007, (pp. 418-428).
Ericsson, U.B., et al., "Thermofluor-based high-throughput stability optimization of proteins for structureal studies", Analytical Biochemistry 357 (2006) (pp. 289-298).
N. Harn, et al., "Highly Concentrated Monoclonal Antibody Solutions: Direct Analysis of Physical Structure and Thermal Stability", J. of Pharmaceutical Sciences, vol. 96, No. 3, Mar. 2007, (pp. 532-546)—XP-002591475.
R. Parti, et al., "Evaluation of thermal stability of monoclonal antibody formulations by fluorescence spectroscopy" BIOTEC 2048.
Busby, T.F., et al., "Thermal stability and ligand-binding properties of human plasma $\alpha_2$-acid glycoprotein (orosomucoid) as determined with fluorescent probes", BBA, 871 (1986) (pp. 61-71)—XP009061712.

(Continued)

*Primary Examiner* — Maureen Wallenhorst
(74) *Attorney, Agent, or Firm* — Whitman, Curtis & Cook, P.C.

(57) ABSTRACT

In a first aspect, provided herein is a method of determining assembly, homogeneity and/or thermodynamic stability of biological macromolecular complexes. In particular, the method allows determining maximum stability of the complexes based on fluorescence changes at an appropriate wavelength as a function of temperature whereby the fluorescence changes reflect the status of assembly, homogeneity and/or thermodynamic stability of the biological macromolecular complexes. The method is based on identifying two state and multistate unfolding fluorescence curves as a function of temperature by fitting the curves according to a multistate unfolding model. In addition, a computer program and a computer program storage medium as well as an apparatus and a system is provided for determining the assembly, homogeneity and/or thermodynamic stability of biological macromolecular complexes.

18 Claims, 4 Drawing Sheets

(56) References Cited

OTHER PUBLICATIONS

Benjwat, S., et al., "Monitoring protein aggregation during thermal unfolding in circular dichroism experiments", Protein Science (2006) 15 (pp. 635-639).

Bischop, J.C., et al., "Thermal Stability of Proteins", Ann. NY Acad. Sci. 1066 (2005) (pp. 12-33).

Backmann, J., et al., "Thermodynamics and Kinetics of Unfolding of the Thermostable Timeric Adenylate Kinase from the Archaean Sulfolobux acidocaldarius", J. Mol. Bio. (1998) 284 (pp. 817-833).

* cited by examiner

METHODS FOR ANALYZING BIOLOGICAL MACROMOLECULAR COMPLEXES AND USE THEREOF

In a first aspect, the present invention relates to a method of determining the assembly, homogeneity and/or thermodynamic stability of biological macromolecular complexes. In particular, the method allows determining maximum stability of said complexes based on fluorescence changes at an appropriate wavelength as a function of temperature, whereby said fluorescence changes reflect the status of assembly, homogeneity and/or thermodynamic stability of the biological macromolecular complexes. Said method is based on identifying two state and multistate unfolding fluorescence curves as a function of temperature by fitting said curves according to a multistate unfolding model. In addition, a computer program and a computer program storage medium, as well as an apparatus and a system is provided for determining the assembly, homogeneity and/or thermodynamic stability of biological macromolecular complexes.

PRIOR ART

Macromolecular complexes, for example biological macromolecular complexes are supramolecular assemblies of different or identical moieties. For example biological macromolecular complexes are assemblies of identical or different biomolecules even of different types of biomolecules. Such biomolecules include proteins, nucleic acids, lipids and sugars. Typically, the macromolecular complexes are formed under specific conditions present in the natural environment, like the living organism. Said macromolecular complexes are crucial for the survival of living organisms and have key functions in various biochemical pathways. A key to the mechanistic understanding how these macromolecular complexes conduct their tasks, is the knowledge about their three dimensional structure. One major obstacle to study the structure and, in particular, the function of macromolecular complexes is the compositional complexity thereof and often the relative instability of said structures, in particular, when being isolated from the natural environment. That is, during purification and in the purified state or when expressed recombinantly or produced synthetically, structure determination and correct formation and assembly of the macromolecular complexes is difficult. That is, ongoing research in the biological sciences reveals that macromolecules in general do not act in isolation but instead are organized into supramolecular assemblies. These modules called macromolecular complexes or molecular machines are the active species, which perform biochemical reactions essential to maintain cellular homeostasis. Molecular machines or macromolecular complexes, in the following referred to macromolecular complexes or, generally, as complexes can be divided into three major classes, those composed of protein only, such consisting of protein and nucleic acid as well as integral membrane complexes.

Irrespective of the nature of the macromolecular complex, it is imperative to determine its three-dimensional structure to gain mechanistic insight into the respective mode of action within cells. To this end, recent advances, such as "TAP-tagging" and recombinant multiprotein expression techniques have made the biochemical purification of many macromolecular complexes technically feasible. Despite tremendous advances in the capability to isolate and reconstitute cellular molecular machines, structural information about them remains scarce. This discrepancy is likely due to biochemical intricacy, which is inherent to these complexes and limits purification yields. Additionally, most molecular machines are labile and often conformationally heterogeneous assemblies upon purification. However, most purifications schemes employ a limited set of buffer systems, like phosphate buffered saline (PBS), Tris buffered saline (TBS) or HEPES buffered saline (HBS). That is, purifications schemes do not cope with the most suitable conditions for purification to allow purification of biological macromolecular complexes, whereby said complexes are in the form as present in its natural environment, namely in the cellular environment.

Moreover, the isolated macromolecular complexes are typically quite labile and, thus, a need for stabilized complexes or complexes having improved stability is immanent. Thus, the stability of many purified macromolecular complexes, in particular, biological macromolecular complexes needs to be optimized at the earliest possible step during complex isolation and purification to make these assemblies amenable to structural biology and suitable for investigation of functionality etc.

It is generally known that protein stability depends on the buffer system. The pH, ionic strength, salts and its concentration in solution, additives, ligands, and the dielectric constant and viscosity influence the stability of the complexes. A simple method to determine the stability of any macromolecular species is to measure its unfolding behaviour in any given solute in response to an incremental increase in temperature. This can be accomplished by either differential scanning calorimetry (DSC) or differential scanning light scattering (DSLS) methods. A third possibility is to perform thermal unfolding in the presence of a dye, whose fluorescence is quenched in polar environments but strongly emits a fluorescent signal when exposed to hydrophobic surroundings like the hydrophobic core of proteins upon unfolding. This method is known as the Thermofluor method or differential scanning fluorometry (DSF). These methods yield to high-throughput settings and have also been used to identify stabilization conditions for single-domain proteins in the presence of various buffer conditions and small molecules. Recently a Thermofluor method has been described in WO 2010/109204 relating to an analytical method of determining thermal stability. The method described therein allows determining stabilizing conditions for single-domain proteins and is based on determining the melting temperature $T_m$ of said proteins only. However, it is identified therein that in complexes, i.e. multi-domain proteins, individual portions of the protein can melt independently giving rise to multiple $T_M$'s. More recently, Kopec J., and Schneider G., J. Structural Biol. 2011, doi: 10.1016/J.JSB 2011.04.006, discussed the comparison of fluorescence and light scattering based methods to access formation and stability of protein-protein complexes. Therein, DSLS and DSF methods have been applied to identify stabilizing conditions for proteins. In particular, a comparison of the two methods was applied for optimization of buffer conditions of protein-protein complexes. However, these methods described therein are based also on determining the $T_M$ of the protein-protein complexes only.

The simplicity and low sample requirements of DSF would make said method particularly useful for determining macromolecular complex stability. However, except for the recent disclosure of Kopec et al where a protein-protein complex was analyzed, said method has not been deemed useful for multi-domain proteins and molecular machines, on the basis that each individual domain/subunit would unfold independently giving rise to polyphasic unfolding curves. Such curves would not contain information on complex stability but would contain information on stability of the individual components only.

Thus, there is an ongoing need for methods and systems allowing determination of assembly, homogeneity and/or thermodynamic stability of biological macromolecular complexes. Said method should be particularly useful for identifying stabilizing conditions for said macromolecular complexes, thus, allowing further functional analysis of said complexes.

BRIEF DESCRIPTION OF THE PRESENT INVENTION

The present invention aims to provide a new method of determining the assembly, homogeneity, and/or thermodynamic stability of biological macromolecular complexes. It has been recognized that calculating the apparent melting temperature of macromolecular complexes is not sufficient to analyze stabilizing conditions and to optimize said stabilizing conditions. In contrast it is required to improve existing methods by identifying apparent two-state unfolding fluorescence curves of the sample as a function of temperature by fitting said curves according to a multi-state unfolding model preferably in the range of a two state to six state model. Fitting is performed by e.g. the Levenberg-Marquardt Algorithm according to the physical parameters of the unfolding model to obtain transitional unfolding curves. Best fitting curves are then used for further processing and a two-state model is assumed only if the difference of the data to the best fitting model is negligibly small.

Thus, in a first aspect a method of determining the assembly, homogeneity, and/or thermodynamic stability of biological macromolecular complexes is provided comprising the steps of
  providing complexes of one or more biological macromolecules in a sample containing a buffer system and a fluorescence dye;
  stepwise increase in temperature of said sample at a rate suitable for measuring fluorescence of said sample after thermal equilibration, thereby determining the fluorescence at an appropriate wavelength as a function of temperature as fluorescence curves, whereby said fluorescence reflects the status of assembly, homogeneity and/or thermodynamic stability of said complex;
  calculating the assembly, homogeneity, and/or thermodynamic stability of said complex based on:
    a) identifying apparent two state unfolding fluorescence curves of the sample as a function of temperature by fitting said curves according to a multistate unfolding model from two state to six state model, e.g by determining the unfolding state based on the Levenberg-Marquardt Algorithm for obtaining transitional curves and $X^2$ minimization and comparing said curves to perfect two-state curves;
    b) calculating the slope of said transitional curves at the inflection point in a two-state model;
    c) calculating the melting temperature $T_m$, and/or the enthalpy of unfolding $\Delta H$.

In addition, the present invention provides a method of determining stabilizing conditions of biological macromolecular complexes, like polypeptide complexes comprising the step of comparing the assembly, homogeneity and/or thermodynamic stability of a sample according to the above described method for at least two or more distinct samples and identifying the conditions, wherein the most stabilizing conditions are present.

Moreover, the method according to the present invention allows screening for ligand binding, screening for compounds destabilizing or inhibiting complex formation or stabilizing or promoting complex formation, or for determining the specificity of ligands towards complexes isolated from one organism versus another organism.

In another aspect, the present invention provides a computer program residing on a computer readable form with a programme code for carrying out the method according to the present invention. Furthermore, a system is provided for determining assembly, homogeneity, and/or thermodynamic stability of biological macromolecular complexes, like polypeptide complexes based on DSF comprising a device for DSF and a data processing unit comprising a software or a computer program according to the present invention for carrying out the method according to present invention.

DETAILED DESCRIPTION OF THE PRESENT INVENTION

Figure 1:
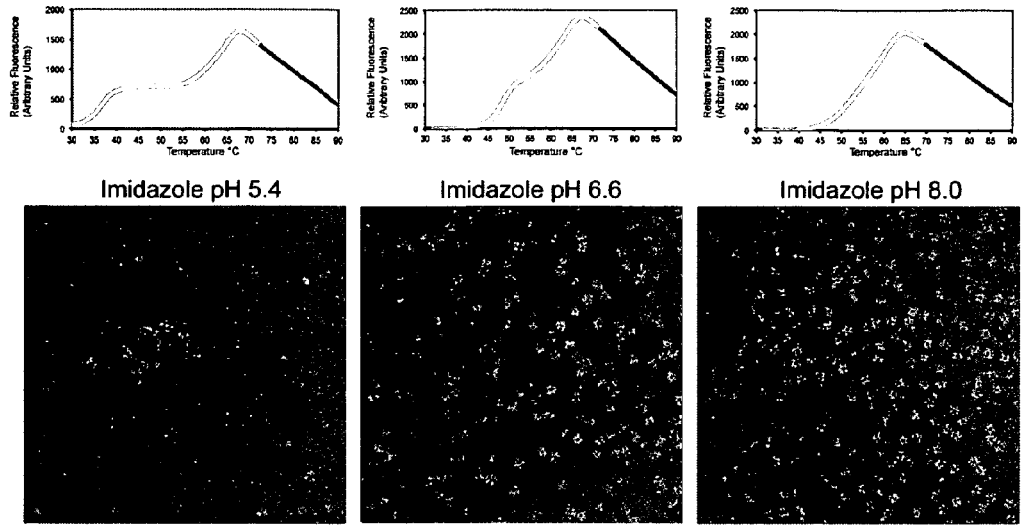
FIG. 1: Comparing the effects of buffer conditions on DSF curves and electron micoscopic images. Sub optimal buffer conditions reveal a multi phase unfolding curve (first two rows). A two state unfolding curve is obtained under optimum buffer conditions (third row). Under those conditions aggregates can no longer be observed in the EM images.

The present invention relates in a first aspect to a method of determining the assembly, homogeneity, and/or thermodynamic stability of biological macromolecular complexes comprising the steps of
  providing complexes of one or more biological macromolecules in a sample containing a buffer system and a fluorescence dye;
  stepwise increase in temperature of said sample at a rate suitable for measuring fluorescence of said sample, thereby determining the fluorescence at an appropriate wavelength as a function of temperature as fluorescence curves whereby said fluorescence reflects the status of assembly, homogeneity and/or thermodynamic stability of said complex;
  calculating the assembly, homogeneity, and/or thermodynamic stability of said complex based on:
    a) identifying apparent two state unfolding fluorescence curves of the sample as a function of temperature by fitting said curves according to a multistate unfolding model from two state to six state model, e.g. by determining the unfolding state based on the Levenberg-Marquardt Algorithm for obtaining transitional curves and $X^2$ minimization and comparing said curves to perfect two-state curves;

b) calculating the slope of said transitional curves at the inflection point in a two-state model;

c) calculating the melting temperature $T_m$, and/or the enthalpy of unfolding $\Delta H$.

As used herein, the term "$X^2$ minimization" is part of the Levenberg-Marquardt algorithm (Numerical Recipes, Third Edition, Chapter 15, p 799).

Further, the term "inflection point of the unfolding transition" is defined as the melting point of the complex.

As used herein, the term "$R^2$" refers to the quality of fitting models to the experimental curves. When $R^2$ is below 0.999 the curve is preferably discarded. It is preferred that $R^2$ is as close as possible to 1.

It is preferred that the fluorescence dye is a solvatochromatic dye. A solvatochromatic dye is a dye whose fluorescence emission is quenched in polar solvent and said dye emits strongly fluorescence when brought to a hydrophobic solvent environment.

That is, when causing gradual unfolding by raising the temperature, solvent exposition of hydrophobic residues of the biological macromolecular complexes happens and, simultaneously, the fluorescence emission signal of the solvatochromatic dyes is increased due to the increasing presence of a hydrophobic solvent environment. The skilled person is well aware of suitable fluorescence dyes. That is, fluorescent dyes suitable for use in thermofluor analysis are well known and include: sypro orange, thioinosine, and N-ethenoadenosine, formycin, dansyl derivatives, fluorescein derivatives, 6-propionyl-2-(dimethylamino)-napthalene (PRODAN), 2-anilinonapthalene, and N-arylamino-naphthalene sulfonate derivatives such as 1-anilinonaphthalene-8-sulfonate (1,8-ANS), 2-anilinonaphthalene-6-sulfonate (2,6-ANS), 2-aminonaphthalene-6-sulfonate, N,N-dimethyl-2-aminonaphthalene-6-sulfonate, N-phenyl-2-aminonaphthalene, N-cyclohexyl-2-aminonaphthalene-6-sulfonate, N-phenyl-2-aminonaphthalene-6-sulfonate, N-phenyl-N-methyl-2-amino naphthalene-6-sulfonate, N-(o-toluyl)-2-aminonaphthalene-6-sulfonate, N-(m-toluyl)-2-aminonaphthalene-6-sulfonate, N-(p-toluyl)-2-aminonaphthalene-6-sulfonate, 2-(p-toluidinyl)-naphthalene-6-sulfonic acid (2,6-TNS), 4-(dicyanovinyl)julolidine (DCVJ), 6-dodecanoyl-2-dimethylaminonaphthalene (LAURDAN), 6-hexadecanoyl-2-(((2-(trimethylammonium)ethyl)methyl)amino)naphthalenechloride (PATMAN), nile red, N-phenyl-1-naphthylamine, 1,1-dicyano-2-[6-(dimethylamino)naphthalene-2-yl]propene (DDNP), 4,4'-dianilino-1,1-binaphthyl-5,5-disulfonic acid (bi-ANS), and DAPDXYL derivatives (Molecular Probes, Eugene, Oreg.).

In one embodiment the dye is Sypro orange available from Molecular Probes Inc. In one embodiment the fluorescence is measured at a wavelength of 530 nm.

Suitable instruments for measuring the emitted light include any second generation real-time PCR system equipped to emit and measure light at appropriate wavelengths, such as a 7900HT fast real-time PCR system available from Applied Biosystems and the CFX96 real-time PCR machine from Biorad.

The temperature for a typical run will be approximately: from 20° C. to 100° C. using a temperature gradient of about 0.02° C./sec, for example based on 384 well block, but may be from 40 to 100° C., if desired. In the case of the 7900HT system, the minimum ramp rate may, for example be 0.02° C./sec (1% power) based on 384 well block. The maximum ramp rate on this system may, for example be 2° C./sec. (100% power) based on 384 well block. Thus a suitable temperature ramp range is about 0.02 to about 2° C./sec.

In one embodiment 2, 3, 4, 5, 6, 7, 8, 9, 10, 20, 30, 40, 50, 60, 70, 80, 90, 94, 96, 100, 150, 200, 250, 300, 350 ore more such as 384 or 1024 protein samples are analysed concomitantly. The instruments can be employed in combination with robotic equipment to automate the process further and increase the number of samples that can be processed without human intervention.

Preferably, the method is based on DSF (differential scanning fluorimetry). DSF can be used as a high-throughput screening technique, which generates significant amount of data that needs to be interpreted allowing automation of a data analysis. It is preferred that data sets or curves are filtered out due to false signals. These false signals or measurements include false results due to air bubbles, pipette errors, dye crystallisation or aggregates of parts of the macromolecular complexes, etc. In addition, it is preferred that the method include a background subtraction for data normalization. In this regard, in another preferred embodiment the curves of fluorescence as a function of temperature are normalized for obtaining transitional curves wherein the lowest local minimum of the curve is set to 0, and the highest maximum of the curve is set to 1000 and experimental values which lie outside the range described by these two data points are excluded from calculation of said curve.

It is well established that the increase in fluorescence is equivalent to the unfolding of the macromolecular complex.

Thus, the next step requires fitting the fluorescence curves of the sample as a function of temperature according to a multi state unfolding model, which includes two, three, four, five, and six states. Under stabilizing conditions an apparent two state unfolding fluorescence curve is obtained. These fitted curves are also referred to as transitional curves. For example, the fitting is performed by using the Levenberg-Marquardt-Algorithm and $X^2$ minimization. Moreover, it is preferred that the similarity to perfect two-state curves is measured based on determining $R^2$ to two-state.

Moreover, in a preferred embodiment, the method includes calculating the slope of the transitional curves at the inflection point in a two-state model and, in addition or alternatively, it is preferred that the temperature $T_m$ and/or the enthalpy of unfolding, $\Delta H$, is calculated. The skilled person is well aware of suitable means and methods for calculating the respective parameters.

Moreover, in a further preferred embodiment, the method includes the step wherein the experimental pH values are determined at the inflection point of the unfolding transition using the $\Delta pK_A/T$ values of the buffer system for the curves showing the fluorescence of an appropriate wavelength as a function of temperature.

It is particularly preferred that the $\Delta H$ is calculated based on non-linear fitting the slope of the unfolding transition. In this case, $\Delta H$ describes the weighted mean of all unfolding and dissociation enthalpies.

For further analysis, the method of the present invention comprises determining stabilising conditions of biological macromolecular complexes, like polypeptide complexes, comprising the steps of comparing the assembly, homogeneity and/or thermodynamic stability of a sample as identified according to a method of the present invention for at least two or more distinct samples and identifying the conditions when the most stabilising conditions are present.

It is preferred, that the curves for identifying the most stabilising conditions are sorted heuristically for predetermined parameters. That is, the method according to the present invention allows identifying the most stabilising conditions for a biological macromolecular complex. Hence, this method is particularly useful for determining stabilizing buffer conditions for said complexes, in particular, for isolation and technical analysis of these complexes.

In a preferred embodiment, the complexes comprise proteins, nucleic acids, sugar, and/or lipids. For example, protein/protein complexes can be examined for assembly, homogeneity and thermodynamic stability. Moreover, the inventors successfully analyzed protein-nucleic acid-complexes.

In another preferred embodiment, the curves are sorted heuristically for predetermined parameters. In particular, it is preferred to select the predetermined parameters in the following order: Result of the multiphase unfolding model fit to the experimental data, fitting result to perfect 2-state model, $\Delta H$ of unfolding for 2-state model, $T_m$ for 2-state model, $\Delta H$ of best-fit model, $T_m$ of best-fit model and the enclosed area beneath the lowest local minimum and the highest local maximum of the transition curve.

Thus, it is possible to determine easily and conveniently by using high throughput methods stabilizing and destabilizing conditions of biological macromolecular complexes.

The method may be used for different approaches. For example, by using the method according to the present invention it is possible to screen ligand binding. That is, by observing and comparing the fluorescence curves, it is possible to identify binding of ligands to said complex. Moreover, the method allows for screening for compounds destabilizing or inhibiting complex formation. On the other hand, the method according to the present invention allows for screening for compounds stabilizing or promoting complex formation. Moreover, the present invention allows identifying specificity of ligand binding to complexes across different organisms. This may be of particular interest e.g. in the field of developing antibiotics or other compounds which should display an effect in one organism but not display said effect in another organism, e. g. having an effect on a pathogen but not on the host.

Another advantage of the method according to the present invention is the fact that it is suitable for high-throughput screening which in turn demands only small quantities of the sample.

Surprisingly, it has been determined that biological macromolecular complexes being composed of various components e. g. of at least 2, 3, 4 or even more different components can be analyzed by applying the differential scanning fluorimetry technology. Thus, it is possible to provide these biological macromolecular complexes for use in screening methods for new active ingredients, e. g. new therapeutics, wherein these macromolecular complexes are involved.

In another aspect, the present invention provides a computer program residing on a computer readable medium, with a program code for carrying out the method according to the present invention. Further, the present invention provides a computer program, which, when it is riding on a computer or is loaded on a computer, causes a computer to perform a method according to the present invention.

In addition, the present invention provides a computer program storage medium comprising a computer program according to the present invention.

Another embodiment relates to an apparatus comprising the computer readable storage medium containing program instructions for carrying out the methods according to the present invention.

Finally, the present invention provides a system for determining assembly, homogeneity and/or thermodynamic stability of biological macromolecular complexes, like polypeptide complexes based on differential scanning fluorimetry and a data processing unit comprising a software or a computer program according to the present invention for carrying out the method according to present invention.

Not to be bound to theory, thermofluor assays are based on the environment dependent fluorescence of the used dye. E.g., while SYPRO-orange as a representative of a suitable fluorescence dye, shows a low quantum yield in polar environments it becomes hyper fluorescent in hydrophobic surroundings. During the assay proteins unfold and expose hydrophobic patches at increased temperature leading to an increase in fluorescence. Upon further increase in temperature this is followed by fast aggregation hiding the previously exposed hydrophobic patches resulting in a lower fluorescence signal. So far the obtained DSF curves were interpreted by non-linear regression of curves to a simple Boltzmann model to determine the inflection point during fluorescence increase. This determines the melting point of the protein and was used as readout for the stabilization of single chain proteins (Niesen, F. H., et al., (2007), 2, 2212-2221). The readout of the melting point only is however, not sufficient for protein complexes. This is also recognized in WO 2010/109204 identifying that for complex, multi-domain proteins, individual portions of the protein can melt independently giving rise to multiple Tm's.

Assuming the described behavior three different species of the dye can be found at any time point in solution: The free dye with a maximal fluorescence of $F_0$, the dye bound to the native state of the protein with a maximal signal of $F_N$, meaning all native protein is native and dye bound and the dye bound to the unfolded protein corresponding to $F_U$. At every time point the measured flourescence signal can be described by the sum of the signal portions emitted by those three species:

$$F = f_N F_N + f_U F_U + F_0 \tag{1}$$

where $f_N$ respectively $f_U$ are the fractions of The unfolded and the folded protein state. Since the dye is in large excess over the protein, $F_0$ does not change during the course of the experiment and can be simply subtracted in experiments by performing a baseline experiment. $F_0$ can thus be ignored in the following.

Assuming a simple two state model described by the equilibrium constant $K = f_U / f_N$ this results in $$F = \frac{F_N + F_U K}{1 + K} \tag{2}$$

The performed experiments are temperature dependent and, therefore as well are all equation parameters. For the K using van't Hoff's Isotherm this leads to:

$$F = \frac{F_N(T) + F_U(T) e^{-\frac{\Delta G_{U-N}}{RT}}}{1 + e^{-\frac{\Delta G_{U-N}}{RT}}} \tag{3}$$

Assuming that the unfolding entropy is temperature independent in the measurement range this yields a slight variation of the Clarke-Fersht equation (Clarke, J., and Fersht, A. R. (1993), Biochemistry 32, 4322-4329)

$$F(T) = \frac{F_N(T) + R_U(T)e^{-\frac{\Delta H_m}{RT}\frac{(T-T_m)}{T_m}}}{1 + e^{-\frac{\Delta H_m}{RT}\frac{(T-T_m)}{T_m}}} \quad (4)$$

where ΔH describes the unfolding enthalpy and $T_m$ the melting temperature at which the fraction of native and unfolded state are equal. $F_N(T)$ describes the initial fluorescence of the screen and can be approximated to be linear for most cases. Detergents, air bubbles or aggregates in the solution as well as exposed hydrophobic patches in the native conformation of a complex can lead to deviations of the linear behavior. In those cases different approximations are required. The initial high signal introduced by detergent resembles very good the temperature dependence of the critical micellar concentration of the detergent and is therefore corrected in a similar way as $2^{nd}$ order polynomial. Air bubbles or aggregates result in increased light scattering. Since the correction of these affects would introduce a number of unknown parameters into the model. Curves showing these effects are simply neglected from hereon. $F_U(T)$ describes the aggregation behavior. Since during the course of the experiment the temperature is increased the aggregation rate is also altered stepwise. This makes an accurate description of this region of the curve impossible with the obtained data. Therefore the course of the aggregation as single exponential has been only approximated.

In view of the above, one would arrive at the formula (5)

$$F(T) = \frac{m_N T + n_N + Q e^{-rT} F_U e^{-\frac{\Delta H_m}{RT}\frac{(T-T_m)}{T_m}}}{1 + e^{-\frac{\Delta H_m}{RT}\frac{(T-T_m)}{T_m}}} \quad (5)$$

The meaningful parameters in here are $T_m$, the melting temperature of the protein—a measure for the unfolding entropy and $\Delta H_m$ the unfolding enthalpy, where a high $T_m$ as well as high $\Delta H_m$ can be found for stabilizing conditions. As accurate description of protein stability one needs to extrapolate the free unfolding enthalpy $\Delta G_{U-N}$ to temperatures desired for structural analysis If the change in heatcapacity during the unfolding process $\Delta C_p$ is known, this can be done by Matouschek, A., et al., (1994), Protein Engineering 7, 1089-1095.

$$\Delta G_{U-N}(T) = \Delta H \frac{T_m - T}{T_m} - \Delta C_P \left[ T_m - T + T \cdot \ln\left(\frac{T}{T_m}\right) \right] \quad (6)$$

For protein-protein complexes more dye states as previously used have to be assumed. In case of complexes every dye can be bound to every individual folded intermediate as well as every unfolded component. Equation (1) changes than to:

$$F = \sum_{i=1}^{n}(f_{N,i}F_{N,i} + f_{U,i}F_{U,i}) + F_0 \quad (7)$$

In principle three different behaviors of the complexes can be assumed now. First the complex disassembles very rapidly due to temperature increase and the components unfold independently. This would lead to a sum of individual unfolding curves and probably multiphasic transitions. Secondly the complex could disassemble slowly while some already dissociated components already unfold. This would lead to the described multiphasic behavior superimposed with a possibly multiphasic disassembly. In the most extreme case disassembly of the whole complex as well as unfolding of its components happens fully cooperative meaning at the same time. This would lead to two-state transitions.

In case of no cooperativity the individual components will unfold independently from each other which can simply be described analogy to equation (3) as:

$$F(T) = \sum_{i=1}^{n} \frac{F_{N,i}(T) + F_{U,i}(T)e^{-\frac{\Delta H_{m,i}}{RT}\frac{(T-T_{m,i})}{T_{m,i}}}}{1 + e^{-\frac{\Delta H_{m,i}}{RT}\frac{(T-T_{m,i})}{T_{m,i}}}} \quad (8)$$

where $\Delta H_{m,i}$ describes the sum of unfolding and dissociation enthalpy concerning one component.

In general every curve must be describable by the superimposition of the disassembly equilibrium of the complex over the unfolding of the individual components given by:

$$F(T) = \sum_{i=1}^{n} \frac{F_{N,i}(T) + F_{U,i}(T)e^{-\frac{\Delta H_{m,i}}{RT}\frac{(T-T_{m,i})}{T_{m,i}}}}{1 + e^{-\frac{\Delta H_{m,i}}{RT}\frac{(T-T_{m,i})}{T_{m,i}}}} \frac{K_{dis}(T)}{1 + K_{dis}(T)}, \quad (9)$$

with $$K_{dis}(T) = e^{-\frac{\Delta H_{dis}(T-T_m)}{RT T_m}}$$

In an extreme case n=1 in equation (8) and (9) leading to an analogue of equation (4). This means total cooperativity of unfolding and disassembly of the complex which is feasible, since the physical nature of forces providing complex stability is equal to those providing a stable fold of a single domain. Under ideal circumstances one can therefore assume that the disassembly of a complex and the unfolding of its components happen concertedly. Equation (4) then becomes suitable for the description of this assumption, with the difference that ΔH describes now the weighted mean of all unfolding and dissociation enthalpies. In consequence n can be used as a measure for cooperativity and is therefore an important parameter for the analysis.

From the above, it is clear that simple analysis of the thermal shift for protein complexes is not sufficient. In the first two described cases the apparent $T_m$ is only a weighted average resulting from several superimposed unfolding curves and gives no information about the complex stability. However, this is also visible in the apparent ΔH values and therefore in the steepness of the curve. Measuring ΔH is thus a valuable tool for the estimation of the information content of $T_m$. A shift of $T_m$ is therefore only meaningful when the steepness of the curve increases or is constant.

30 Complexes ranging in size between 100 kDa up to 5 MDa were analyzed so far, see below.

In all cases complexes were mixed with highly concentrated buffer substances and the dye for consecutive measurement of unfolding curves. The resulting curves were fitted to all described models and further analyzed. Furthermore negative stain TEM images of the complexes in equal conditions were taken. Buffer conditions resulting in multiphasic curves or curves only fitting to equations (8) or (9) with high n resulted mostly in aggregated or disrupted samples as seen by EM.

FIG. 1 shows an example of such a condition. In contrast curves with low n, high ΔH and high $T_m$ revealed a monodisperse distribution of intact particles in electron microscopic images (see FIG. 1, third row).

Although a complete unfolding cooperativety seems very unlikely for large heterogeneous complexes, we found appropriate conditions revealing two state unfolding behavior for all complexes tested so far. For full cooperativity, disassembly corresponds in an inverse manner to a cooperative assembly of the complexes.

For further validation of the theory, complexes were treated with the GraFix methodology (Kastner, B.,et al., (2008), Nat. Methods 5, 53-55.), in which the complexes are slightly fixed with glutaraldehyde without introduction of harsh structural changes or damaging of the structural integrity of the complexes. This method was found to also increase complex stability as well as leading to monodisperse complexes. As control for our theory we subjected GraFix treated samples to DSF experiments and analyzed with our method. It was found that in all cases Grafix treated samples showed mostly apparent two state curves with increased $T_m$ while $\Delta H$ remained constant. This is in good agreement with the assumption that the slight chemical fixation by GraFix only introduces a few crosslink and thus lowers the entropy difference between assembled and disassembled state while the major part of the enthalpic contribution remains unchanged.

Data Analysis—Method Features

DSF can be used as a high-throughput screening technique, which generates significant amount of data that needs to be interpreted. Thus, it is desirable to automate the data analysis and interpretation of DSF curves to the greatest possible extent. The method according to the present invention in form of a stand alone software tool based on the theoretical background introduced above which allows very fast data processing with minimum user interaction required has been developed.

The software requires two input files. One file contains the DSF data obtained from a real time PCR machines. The second input is a simple text file specifying the buffer conditions for each DSF curve in the raw data. Initial processing of the data includes automated features such as background subtraction, data normalization, air bubble detection and pipetting error correction as well as an automatic identification of non relevant datasets.

The data analysis is done via a fast curve fitting with the method according to the present invention for two to six states for all input datasets using the Levenberg-Marquardt algorithm (Marquardt, D. W. (1963), Journal of the Society for Industrial and Applied Mathematics 11, 431-441.) with $X^2$-measurement.

Filtering and Hierarchical Sorting of Conditions.

In order to efficiently find DSF curves describing stabilizing conditions a filtering and hierarchical sorting approach may be applied.

So far Thermofluor-based assays have relied exclusively on $T_m$ values for data evaluation. This is a reasonable approach for samples exhibiting perfect two-state unfolding behavior since $\Delta H$ must be almost equal for all conditions according to Hess's law. However, for protein complexes many DSF curves resemble this two state models but their increase in fluorescence can be less steep. Meaning a smaller $\Delta H$ and therefore only a mean of different enthalpic contributions. Taking only $T_m$ values into account, a shallow curve will lead to misleading results because its $T_m$ value will be shifted to meaningless higher values. The shallow curve shape is a result of superimposition of several unfolding curves that can be attributed to different species of the complex in solution. It is therefore an indication of increased sample heterogeneity. To avoid such misinterpretations the DSF curves are presorted according to the steepness of the curve, which is described by the apparent $\Delta H$.

Altogether, currently an algorithm with three steps of data preparation and filtering and another three steps of hierarchical sorting and dynamical thresholding for the fully automated search for the DSF curves representing the most stabilizing conditions are used.

Filtering Steps:
(1) For all curves the background is subtracted and they are normalized to a range between 0 and 1000. The least local minimum of the curve is set to 0 and the highest local maximum is set to 1000, respectively. All values in between this interval are normalized within the range of 0 to 1000; all values out of this interval are discarded.
(2) Curves of samples containing air bubbles are identified by the average incline of the curves fluorescence values in the interval from the first data point to the lowest local minimum of the curve. All DSF curves with a strong negative slope are discarded.
(3) Each curve is fitted to each model from two-state to six-state and the best fit, regarding to $R^2$ measurement is detected. If the best fit's $R^2$ is below 0.999 this curve is discarded.

Preferred Sorting and Thresholding Steps According to the Present Invention:

For quantifying the quality of a fit the $R^2$ measurement is used.

$$R^2 = 1 - \frac{SS_{err}}{SS_{tot}} \qquad (10)$$

Where $R^2$ is one minus the quotient of the sum of squares of residuals ($SS_{err}$) divided by the total sum of squares ($SS_{tot}$). With $$SS_{tot} = \sum_i (y_i - \overline{y})^2$$

and $$SS_{err} = \sum_i (y_i - f_i)^2$$

where $$\overline{y} = \frac{1}{n}\sum_i^n y_i$$

and $y_i$ are the values of the dataset and $f_i$ the corresponding values form the fitted model.

The parameters for thresholding can be given as percentage value and the order of appliance can be set, for example:
(1) All remaining curves are sorted by their $R^2$ value to the two-state-model and the best 50% (rounded up) of the curves are passing to the next step.
(2) Now the remaining curves are sorted by their $\Delta H$ values and again only the best 50% (rounded up) are passing to the next level.
(3) In this last step the curves are sorted by their $T_m$ values and only the best 50% (rounded up) represent the curves of the samples with the most stabilizing conditions.

Result of the Algorithm:

Up to three curves will remain after this algorithm, representing the most stabilizing conditions for the specimen.

The described ordering system has been evaluated by electron microscopy. Top graded curves always resulted in monodisperse distributions of intact particles on the EM grid. This is especially true if the sample is additionally subjected to the GraFix-methodology in the resulting stabilizing buffer (Kastner et al., see above).

Additional Features

The method according to the present invention can additionally correct for the most common problems in the thermofluor-technique, due to pipetting errors, bad samples or other reasons, the sample contains air bubbles, dye crystals or protein aggregates. All of these lead to light scattering and therefore to high initial signals. The software can detect those curves and neglect them in the further analysis. Similar effects are found in detergents due to micelle formation. In those cases the software will correct those curves by subtraction of a $2^{nd}$ order polynomial.

Moreover the method according to the present invention can correct for temperature induced pH-shifts. Since $pK_A$ values of the buffer substances can tremendously vary with temperature one has to correct for this. The model result parameters for the curve are accurately determined for the melting point. This means that they describe the stability at the pH at the melting point. In dependence of the complex stability the pH difference can be significant and result in misinterpreting the pH of the new desired buffer. This is corrected by linear extrapolation on the melting point using the $\Delta pK_A/T$ values provided by the substance supplier. The impact of that on the curve shape is already corrected by $F_U(T)$ fitted as single exponential, since the dependence between $\Delta G_{N-U}$ and pH is linear Tanford, C. (1970), in Protein Chemistry, J. J. T. E. C. B. Anfinsen, and M. R. Frederic, eds. (Academic Press), pp. 1-95.) as well as the one between pH and T.

Furthermore all already established thermoflour variations can be applied now to large protein assemblies. This includes enzymologic binding assays as well as pharmaceutic screens.

Experimental Procedures

Thermofluor Assay

The screen was performed in 20 µL reactions in a 96 well plate (multiplate 96, white, low profile, Biozyme). Each well contained 0.1-1 µM complex supplemented with a 10× SyproORANGE (Invitrogen, Germany) and 2 µL of an appropriate screening plate. Screens for buffer substance and pH were perfomed with pHat screen (Jena Bioscience, Germany) for additives with the Additive Screen HT (Hampton Research, USA). Every plate contained control wells without protein as well as without screening substance. Measurements were performed in a CFX96 Real Time unit (BioRAD, USA) in a temperature range between 30° C. and 95° C. in a step size of 1° C. At each temperature the reactions were left to be equilibrated for 30 seconds. Finally the signal obtained from the HEX-channel was analysed.

Electron Microscopy

Purified complexes were supplemented with the appropriate screening substance incubated for 10 mins and adsorbed onto a custom made carbon film. Images were taken on a CM 200 FEG electron microscope (FEI, The Netherlands) at 160 kV. A4 k×4 k CCD camera (TemCam-F415; TVIPS, Germany) was used at 2-fold binning of the pixels and 86.000× magnification.

For verifying the method according to the present invention, unfolding transitions of the selenocysteine synthase (SelA), a homo-decameric complex with a native molecular weight of 500 kDa, under various buffer conditions of the pHAT Buffer screen in the presence of the fluorescent dye Sypro Orange (Invitrogen) have been recorded. The unfolding transitions have been analysed based on the method according to the present invention. Further, the dispersity of the sample under the respective conditions has been determined by electron microscopy (EM). Under buffer conditions where distinctly polyphasic unfolding transitions were recorded, large aggregates in negative stain EM have been observed (FIG. 1, left row). When partially three-state transitions were recorded, EM images showing partial aggregation (middle panel) have been obtained. In contrast, conditions, which yielded apparently two-state unfolding transitions, showed a mono-disperse field of single particles by EM (right panel). Thus, single thermal unfolding transitions as determined by the method according to the present invention can indeed be obtained for complexes and are indicative of mono-dispersity and stability of macromolecular complexes. These findings are in good accordance with theoretical thermodynamic considerations, which predict that macromolecular complexes do indeed unfold in an apparently two-state manner under stabilizing conditions as outlined above. It is this surprising behaviour of complexes under stabilizing conditions which makes the Thermofluor method in combination with the method according to the present invention a useful tool to optimise macromolecular complex stability in contrast to earlier statements, e.g. in WO2010/109204.

Figure 2:
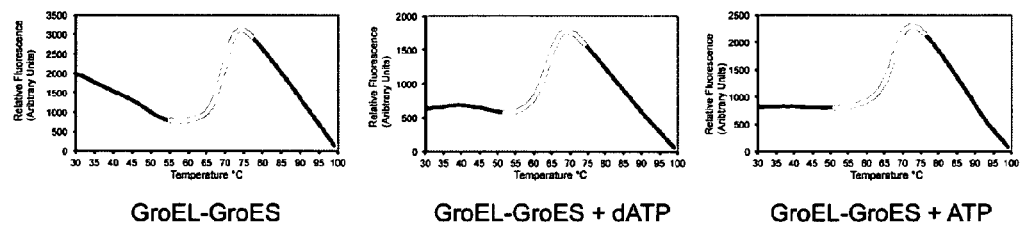
FIG. 2: Formation of GroEL/GroES complex in the absence or presence of dATP or ATP. As shown, GroEL/GroES complexes are formed in the presence of either dATP or ATP.

In a next proof of principle for the validity of the method according to the present invention, it has been determined whether thermal unfolding was suitable to find small molecules, which stabilize molecular machines similarly as has been documented for single-domain proteins (Ericsson et al. 2006, Analytical Biochemistry, 357:289-298). For this the GroEL/GroES (homo-tetradecameric 800 kDa and homo-heptameric 70 kDa, respectively) chaperonin system has been analysed. Two important properties of the chaperonin system have been well documented in the literature (Sigler et al., 1998, Annual Reviews in Biochemistry, 67:581-608; Tang et al., 2006, Cell, 125:908-914). First, GroEL forms a double heptameric ring structure, which exposes hydrophobic residues on one face, where non-native substrate protein can bind. Second, the binding of adenine-nucleotides to GroEL induces a conformational change, which causes the previously exposed hydrophobic residues to be buried and is essential for GroES binding to one face of the GroEL double ring. Therefore, measurements according to the present invention of an equimolar GroEL/GroES should yield a high initial fluorescence owing to the solvent-exposed hydrophobic residues, which gradually decreases upon temperature ramping. In the presence of either dATP or ATP, this high initial intensity is absent and a single—apparent two-state—unfolding transition is observed, indicating formation of the GroEU GroES complex, see FIG. 2. Thus, the method according to the present invention is suitable to determine small-molecule stabilizers of molecular machines.

Next, another abundant class of cellular molecular machines, the nucleic acid-protein complexes have been studied. It has been started with ribosomes which have been extensively studied both by biochemistry and structural biology for several decades. Several well-established protocols exist for the purification of ribosomes from various sources, which yield stable particles amenable to structural biology. We thus purified 80S ribosomes from HeLa cells according to standard protocols and subjected them to the method according to the present invention. HeLa 80S ribosomes are composed of more than 80 proteins and 4 RNAs. Surprisingly, a nearly two-state unfolding behaviour of 80S ribosomes has been obtained with the method according to the present invention.

Figure 3:
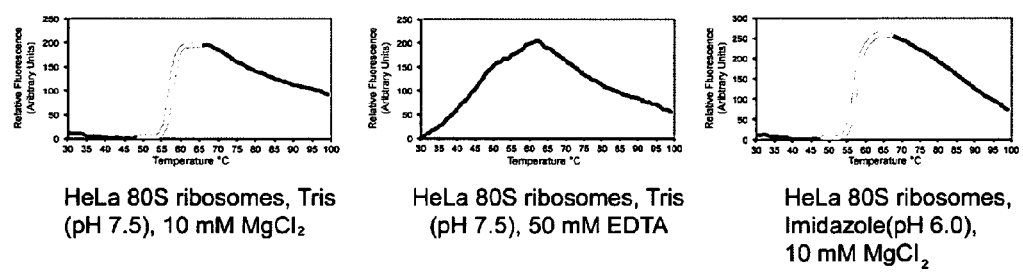
FIG. 3: When treated with 50 mM EDTA 80S ribosomes become unstable and no longer show a two-state unfolding behaviour (middle panel). Optimum stabilizing conditions were found at pH6 in Imidazol and 10 mM $MgCl_2$ (right panel).

To verify if these single transitions corresponded to intact particles we subjected them to gradient centrifugation and subsequent SDS-PAGE. A mono-dispersely sedimenting species of particles with an approximate Svedberg constant of 80S as expected for HeLa ribosomes have been found. Then purified 80S ribosomes have been treated with 50 mM EDTA and subjected to the method according to the present invention. Under these conditions, the divalent Mg ions, which stabilize 80S ribosomes, are titrated away and it is documented that a mixture or ribosomal 40S and 60S subunits are formed. This could be verified by density gradient analysis and according to the present invention yielded polyphasic transitions (FIG. 3). In summary, the method according to the present invention is also suitable to determine and optimize the stability of nucleic acid-protein complexes.

Finally, having provided ample proof that the method of the present invention is suitable for the optimization of macromolecular complex stability, a poorly characterized molecular machine for structural biology has been analysed.

Figure 4:
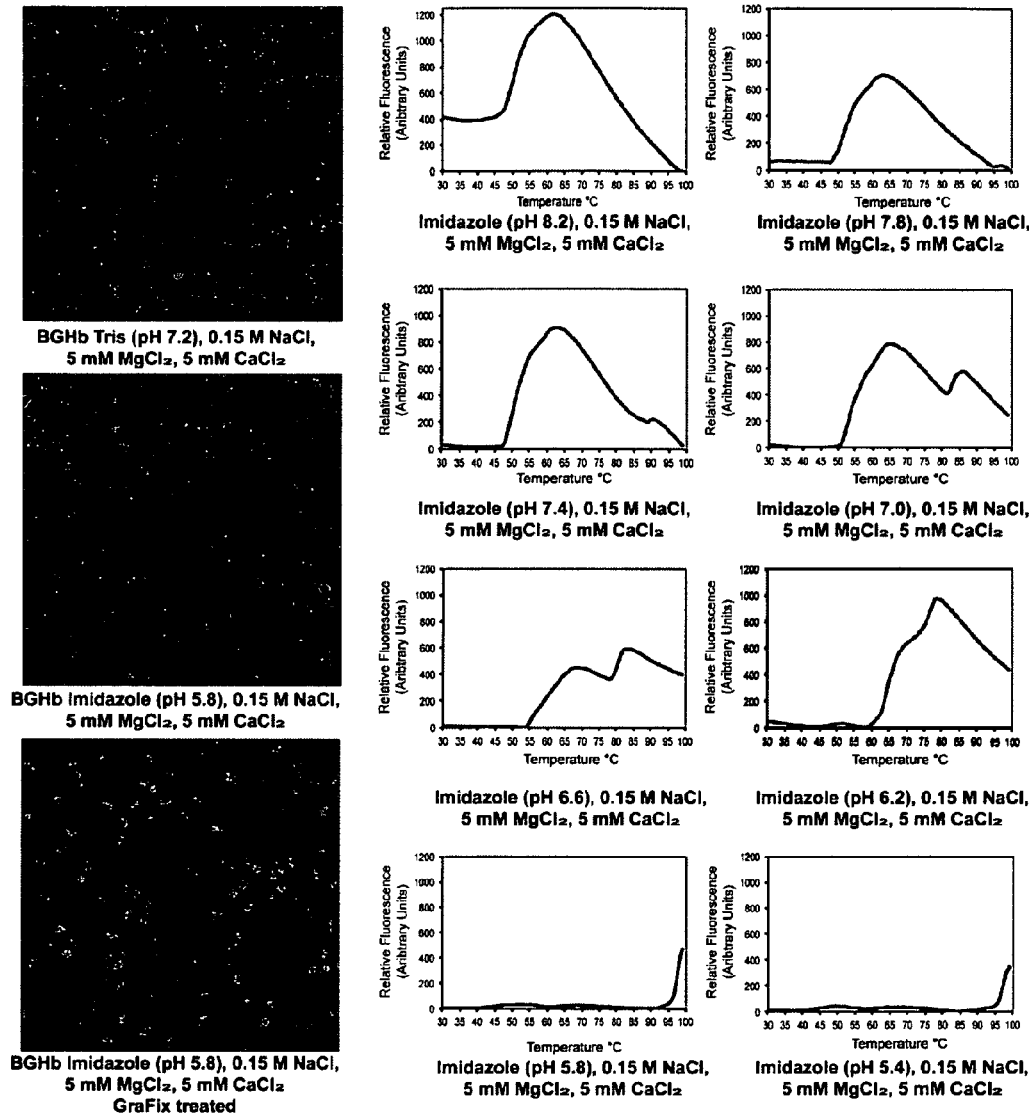
FIG. 4: BGHb (haemoglobin of Biomaphalaria glabrata) being composed of 13 different, cysteine-free globin domains plus a small N-terminal nonglobin domain with three cysteines are analysed for complex formation.

To this end, the haemoglobin of *Biomaphalaria glabrata* (BGHb) has been selected. BGHb is composed of 13 different, cysteine-free globin domains, plus a small N-terminal nonglobin "plug" domain with three cysteines for subunit dimerization (Lieb et al. 2006, PNAS). These subunits are reported to form a quaternary structure of 3×2 disulfide bonded subunits, which form a total mass of about 1.4 MDa. BGHb was purified as previously described (Lieb et al. 2006, PNAS, 103:12011-12016), by anion-exchange chromatography and the aggregation state determined by EM (FIG. 4). Electron micrographs revealed a poly-disperse sample with various degrees of dissociated particles and aggregates. Then BGHb was subjected to the method according to the present invention. A gradual stabilization of BGHb in Imidazole buffer from alkaline to acidic pH values has been observed. In fact, from a pH of 8.2 to pH 5.8 the thermal stability of BGHb was enhanced by 45 Kelvin. Of note, no thermal unfolding transitions for BGHb in any other buffer system in the pHAT screen have been observed, suggesting strong destabilization. Therefore, BGHb has been rebuffered into Imidazole at pH 5.8 and its aggregation state re-evaluated by EM (FIG. 4). In these conditions, clearly discernable single particles of BGHb with some amount of dissociated subunits have been found. When BGHb in Imidazole at pH 5.8 was further subjected to GraFix (Kastner et al., Nature methods, 2008, 5:53-55) EM micrographs with a mono-disperse field of particles have been obtained (FIG. 4), which are clearly amenable to structural biology. Notably, this entire procedure was accomplished within 24 hours. Thus, the method according to the present invention, preferably, in combination with GraFix (Kastner et al., Nature methods, 2008, 5:53-55) has the capacity to turn the course of structure determination projects from hopeless to very promising.

Figure 5:
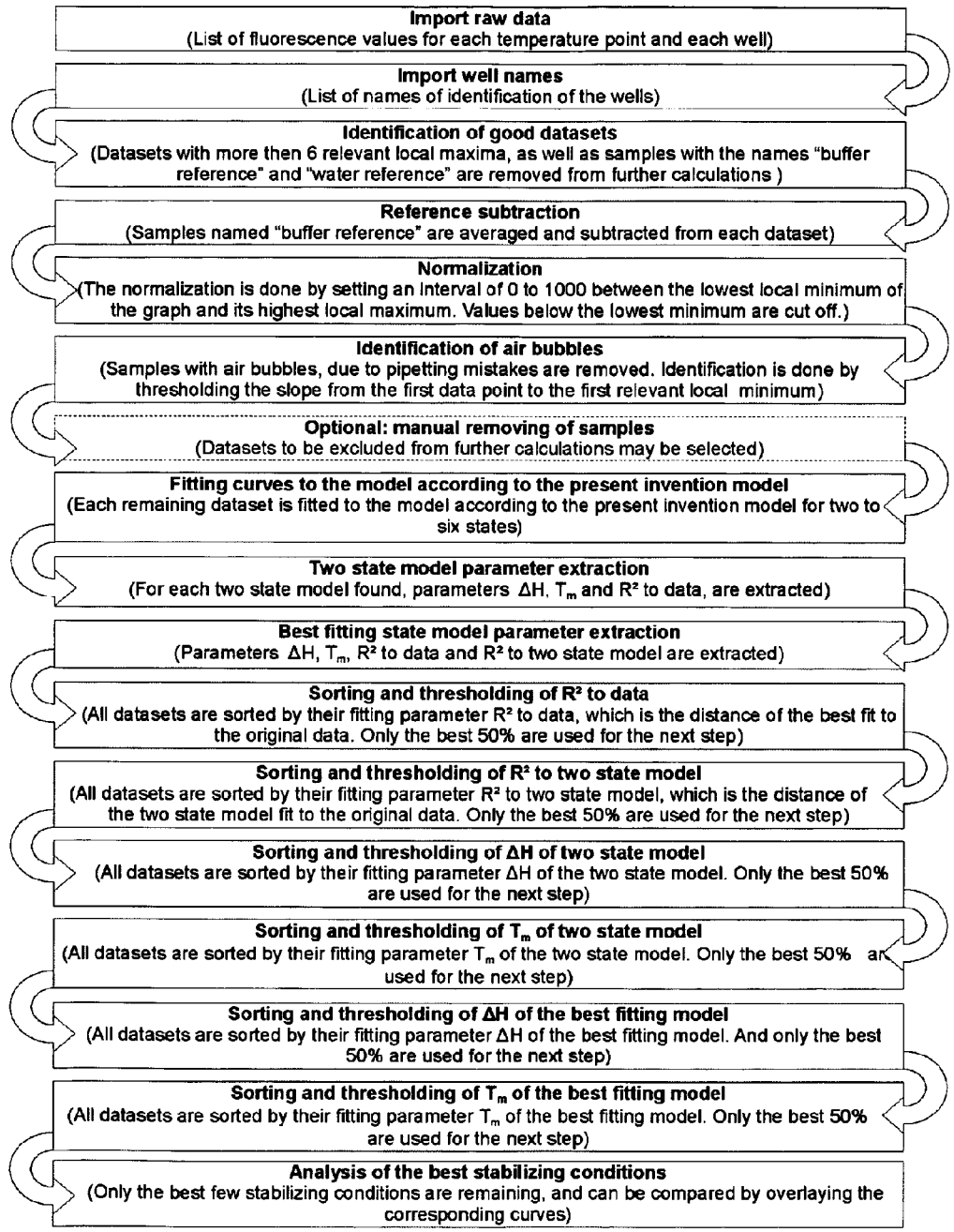
FIG. 5: Shown is a flow chart of the steps performed according to the present invention.
Figure 6:
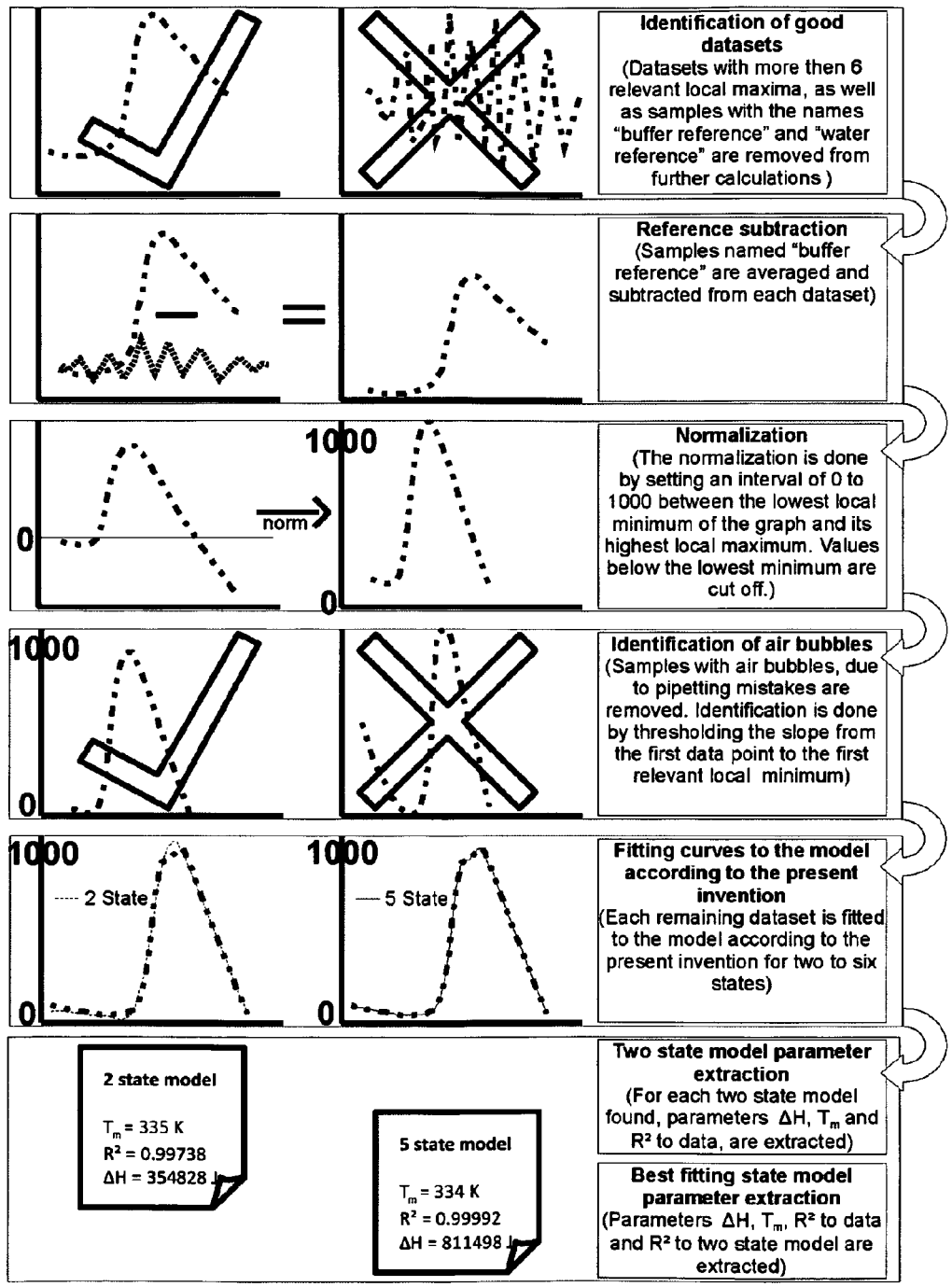
FIG. 6: Shown are curves which are selected or excluded based on the different selection steps according to the present invention. Reference is made to the steps identified in the flow chart shown in FIG. 5.

In FIGS. 5 and 6, the method according to the present invention is detailed in a flow chart and by way of exemplary curves, respectively. The raw data of fluorescence over the temperature of each probe are combined with the respective data information for each probe. Then, data sets with more than six relevant local maxima as well as reference samples or probes are excluded, see also first and second line of FIG. 6.

Subsequently, buffer references are averaged and subtracted from the data set. In addition, the data set are normalized as identified, see also FIG. 6, third line. In addition data sets are excluded that show abnormal structure due to air bubbles or crystallisation, see also FIG. 6, fourth line.

The analysis is continued by fitting the remaining data sets to the model for two to six states according to the present invention. Accordingly, the various parameters are calculated for each fit, in particular for each two state model, see also FIG. 6, fifth or last line. Further, the various parameters for the best fitting model are extracted.

After calculating the various parameters, the data sets are sorted as outlined taking the various parameters into account. Finally, the remaining curves are compared to identify the best stabilizing conditions, e.g. by overlaying the curves.

The invention claimed is:

1. A method of determining the assembly, homogeneity, and/or thermodynamic stability of biological macromolecular complexes comprising the steps of
    providing complexes of one or more biological macromolecules in a sample containing a buffer system and a fluorescence dye;
    stepwise increasing of the temperature of said sample at a rate suitable for measuring fluorescence of said sample after thermal equilibration and measuring the fluorescence of said sample after the thermal equilibration following each stepwise increase in temperature to form a fluorescence curve as a function of temperature, thereby determining the fluorescence at an appropriate wavelength as a function of temperature whereby said fluorescence reflects a status of assembly, homogeneity and/or thermodynamic stability of said complex;
    calculating the assembly, homogeneity, and/or thermodynamic stability of said complex based on:
        a) identifying apparent two state unfolding fluorescence curves of the sample as a function of temperature by fitting said curves according to a multistate unfolding model which includes each of a two, three, four, five, and six state unfolding model to obtain transitional curves and comparing said transitional curves to perfect two-state curves;
        b) calculating a slope of said transitional curves at an inflection point in a two-state model; and
        c) calculating a melting temperature $T_m$, and an enthalpy of unfolding $\Delta H$.

2. The method according to claim 1, wherein the step of calculating the assembly, homogeneity and/or thermodynamic stability of said complex includes identifying transitional curves to be discarded based on a strong negative slope in a first part of the curve.

3. The method according to claim 1, wherein the curves of fluorescence as a function of temperature are normalized for obtaining transitional curves wherein the transitional curve has a lowest local minimum which is set to 0, and the transitional curve has a highest maximum which is set to 1000 and experimental values which lie outside a range described by these two data points are excluded from calculation of said transitional curve.

4. The method according to claim 1, wherein experimental pH values are determined at an inflection point of the unfolding transition using $\Delta pK_A/T$ values of a buffer system for the curves showing the fluorescence of an appropriate wavelength as a function of temperature.

5. The method according to claim 1 wherein the $\Delta H$ is calculated based on a slope of the unfolding transition.

6. The method of determining stabilising conditions of biological macromolecular complexes, comprising the step of comparing the assembly, homogeneity and/or thermodynamic stability of a sample identified according to claim 1 for at least two or more distinct samples and identifying the conditions wherein the most stabilising conditions are present.

7. The method according to claim 6, wherein the transitional curves are sorted heuristically for predetermined parameters.

8. The method according to claim 7 wherein the predetermined parameters are selected in the order: $R^2$ to experimental data, $R^2$ to perfect 2-state model, $\Delta H$ of unfolding for 2-state model, $T_m$, for 2-state model, $\Delta H$ of best-fit model, $T_m$ of best-fit model, and the area beneath the lowest local minimum and highest local maximum of the transition curve.

9. The method according to claim 6, wherein the biological macromolecular complexes are polypeptide complexes.

10. The method according to claim 1, wherein fluorescence curves with light scattering intensities are discarded in advance.

11. The method according to claim 1, wherein the fluorescence curves are based on differential scanning fluorimetry (DSF).

12. The method according to claim 1, wherein the calculation is effected by software.

13. A non-transitory computer programme storage medium which is encoded with a a computer programme with a programme code for carrying out the method according to claim 1.

14. System for determining assembly, homogeneity, and/or thermodynamic stability of biological macromolecular complexes, based on differential scanning fluorimetry comprising a device for differential scanning fluorimetry and a data processing unit comprising a software or a computer programme according to claim 13.

15. The system according to claim 14, wherein the biological macromolecular complexes are polypeptide complexes.

16. Apparatus comprising a non-transitory computer readable storage medium containing programme instructions for carrying out the method according to claim 1.

17. The method according to claim 1, wherein the step of fitting the curves in step a) is performed by determining the unfolding state based on the Levenberg-Marquardt Algorithm for obtaining transitional curves and $X^2$ minimization.

18. A method for identifying buffer conditions allowing further analysis and processing of biological macromolecular complexes, comprising the steps of
   i) providing complexes of one or more biological macromolecules in a sample containing a buffer system and a fluorescence dye;
   ii) stepwise increasing of the temperature of said sample at a rate suitable for measuring fluorescence of said sample after thermal equilibration and measuring the fluorescence of said sample after the thermal equilibration following each stepwise increase in temperature to form a fluorescence curve as a function of temperature, thereby determining the fluorescence at an appropriate wavelength as a function of temperature whereby said fluorescence reflects a status of assembly, homogeneity and/or thermodynamic stability of said complex;
   iii) assessing buffer conditions allowing further analysis and processing by calculating the assembly, homogeneity, and/or thermodynamic stability of said complex based on:
      a) identifying apparent two state unfolding fluorescence curves of the sample as a function of temperature by fitting said curves according to a multistate unfolding model which includes each of a two, three, four, five, and six state unfolding model to obtain transitional curves, and comparing said transitional curves to perfect two-state curves;
      b) calculating a slope of said transitional curves at an inflection point in a two-state model; and
      c) calculating a melting temperature $T_m$, and an enthalpy of unfolding $\Delta H$.

* * * * *